United States Patent
Motoki et al.

(10) Patent No.: US 7,945,081 B2
(45) Date of Patent: May 17, 2011

(54) DIAGNOSIS AIDING SYSTEM

(75) Inventors: Wataru Motoki, Hachioji (JP); Mamoru Umeki, Hachioji (JP); Jiro Okuzawa, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 941 days.

(21) Appl. No.: 11/729,485

(22) Filed: Mar. 29, 2007

(65) Prior Publication Data
US 2007/0230661 A1   Oct. 4, 2007

(30) Foreign Application Priority Data

Apr. 4, 2006   (JP) .................................. 2006-103202

(51) Int. Cl.
*G06K 9/00*   (2006.01)
*G06Q 10/00*   (2006.01)
(52) U.S. Cl. .......................................... 382/131; 705/2
(58) Field of Classification Search ............................ None
See application file for complete search history.

(56) References Cited

U.S. PATENT DOCUMENTS

| 5,917,536 | A | * | 6/1999 | Kunimoto et al. | 347/247 |
| 6,859,288 | B1 | * | 2/2005 | Brackett et al. | 358/1.15 |
| 2005/0078857 | A1 | * | 4/2005 | Park | 382/128 |

FOREIGN PATENT DOCUMENTS

JP   2003-224703   8/2003

OTHER PUBLICATIONS

English abstract of Japanese Application No. 2003-224703.

* cited by examiner

*Primary Examiner* — Brian P Werner
(74) *Attorney, Agent, or Firm* — Cantor Colburn LLP

(57) ABSTRACT

A diagnosis aiding system that photographs an examination subject without a photographing order and generates image data of the examination subject, and thereafter links the image data with the examination subject, includes: an image generating unit that photographs an examination subject and generates data of a photographed image of the examination subject; a switching operation unit to input switching information on an examination subject; and a controller that stores one or more photographed images, of a single examination subject, generated by the image generating unit between input of preceding switching information and input of subsequent switching information via the switching operation unit, linking the one or more photographed images with examination subject information on the single examination subject.

10 Claims, 10 Drawing Sheets

FIG. 3

| RECEPTION NUMBER | PATIENT NAME |
|---|---|
| 01 | TANAKA ICHIRO |
| 02 | SUZUKI JIRO |
| 03 | YAMADA SABURO |
| 04 | YAMAMOTO HANAKO |
| 05 | YAMAMOTO GORO |
| ... | ... |
| ... | ... |
| ... | ... |
| ... | ... |
| ... | ... |
| ... | ... |
| ... | ... |

FIG. 6

EXAMINATION SUBJECT PATIENT

RECEPTION NUMBER 01

TANAKA ICHIRO

DIAGNOSIS AIDING SYSTEM

This application is based on Japanese Patent Applications No. JP2006-103202 filed on Apr. 4, 2006, the entire of which is hereby incorporated by reference.

FILED OF THE INVENTION

The present invention relates to a small-scale diagnosis aiding system that operates corresponding to a workflow of diagnosis in a small-scale medical institution.

BACKGROUND OF THE INVENTION

In large-scale medical institutions, there have been developed large-scale diagnosis aiding systems that aid a series of tasks on a workflow from reception of patients to completion of examination and diagnosis (for example, refer to Patent Document 1: Japanese Patent Publication TOKKAI No. 2003-224703). On a workflow, for example, tasks of (1) registration of reception of patients, (2) examination photographing, (3) inspection of images (confirming the image quality of photographed images) (4) diagnosis (interpretation of photographed images), and (5) accounting, are carried out in different places in this order. In accordance with such a workflow, a diagnosis system distributes processing functions corresponding to respective tasks to a plurality of terminals, and connects the respective terminals via a network to make them collaborate with each other. The tasks include, for example, (1) registration processing of patient information, (2) digitizing photographed images taken by examination photographing (a console function), (3) image processing of photographed images, (4) display processing of photographed images for interpretation of the images (a viewer function), and (5) accounting processing.

With a large-scale diagnosis aiding system, as described above, plural people, such as a doctor, engineer (technician), and reception operator work on plural patients at a same time at separate places. Accordingly, for prevention of miscorrelation between patients and photographed images, and for collaboration between the tasks of there respective workers and collaboration between processings by the respective terminals (work stations), instruction information, which is called photographing order information, is generated in advance at the stage (1).

Photographing order information includes patient information on a patient, photographing information on photographing, such as the photographing date and time and photographing body part, and the like. Based on this photographing order information, a patient as a subject of photographing, photographing body part, and the like can be determined. Further, by storing photographed image data generated by photographing, linking it with the photographing order information, as described above, each photographed image can be identified, according to the photographing order information, and integrated administration cab be achieved.

However, in a small scale medical institution, such as a clinic, a workflow, as described above, is often carried out by a small number of people, such as a doctor and assistant, and there are many cases where a medical doctor alone does all the tasks. In such a case, the doctor does not work on other patients during the time between receiving a patient and completing diagnosis of the patient, and accordingly the doctor rarely miscorrelates patients and photographed images.

If a large-scale diagnosis aiding system, as described above, is applied as it is even in this situation, it is necessary to go through registration processing for issuing photographing order information at the time of reception, which requires a complicated procedure. Further, since the installation space for a system is limited, a functionally-distributed large-scale system, as described above, has not been an optimum one.

For example, in a case of working on patients one by one, photographed images are also generated serially one by one, and thus photographed images are obtained sequentially for patient by patient. Nevertheless, when patients and photographed images are to be linked by photographing order information, as carried out in a large-scale diagnosis aiding system, it is required to determine patients corresponding to respective images one by one, checking with the content of photographing order information, which is inefficient.

An object of the present invention is to provide a diagnosis aiding system that is suitable for a small-scale medical institution and is able to link patients and photographed images efficiently and simply.

SUMMARY OF THE INVENTION

In an aspect of the invention, a diagnosis aiding system that photographs an examination subject without a photographing order and generates image data of the examination subject, and thereafter links the image data with the examination subject, includes:

an image generating unit that photographs an examination subject and generates data of a photographed image of the examination subject;

a switching operation unit to input switching information on an examination subject; and a controller that stores one or more photographed images, of a single examination subject, generated by the image generating unit between input of preceding switching information and input of subsequent switching information via the switching operation unit, linking the one or more photographed images with examination subject information on the single examination subject.

BRIEF DESCRIPTION OF THE DRAWINGS

FIG. 3 is a diagram showing an example of an examination-subject list of patients who are subjects of examination;

FIG. 6 is a diagram showing a patient notification screen displayed on a display, shown in FIG. 5;

DETAILED DESCRIPTION OF THE PREFERRED EMBODIMENT

Figure 1:
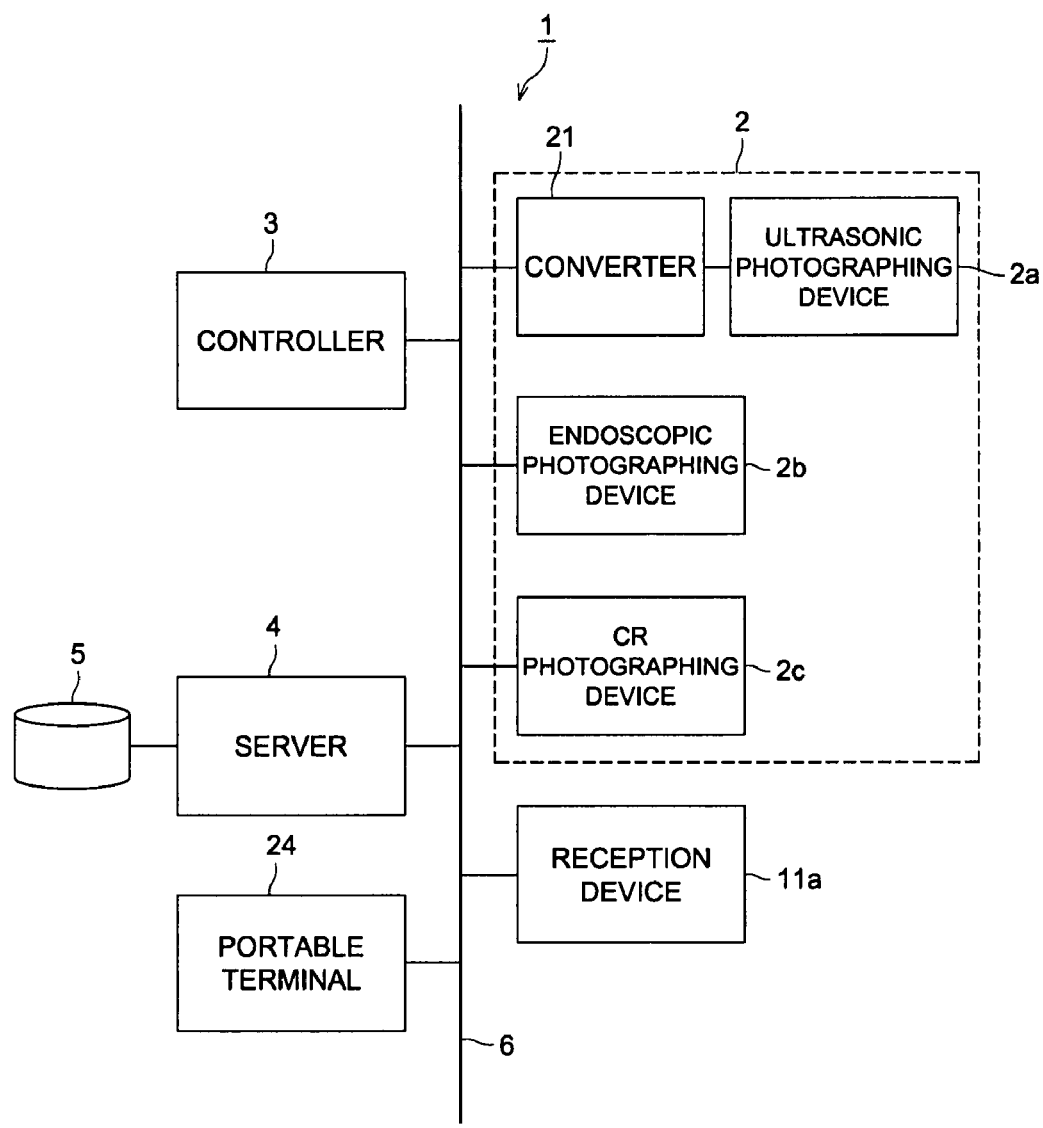
FIG. 1 is a diagram showing a system configuration of a diagnosis aiding system in accordance with the present embodiment.

The present invention includes the following structures.

Item 1.

A diagnosis aiding system, including;

an image generating unit that photographs an examination subject/subjects and generates data of a photographed image/Images of the examination subject/subjects;

a switching operation unit to input switching information on an examination subject/subjects; and a controller that stores one or more photographed images generated by the image generating unit between preceding switching information and subsequent switching information inputted via the switching operation unit, linking the one or more photographed images with examination subject information on an examination subject.

Item 2.

The diagnosis aiding system of Item 1, wherein the switching operation unit is arranged on the image generating unit.

Item 3.

The diagnosis aiding system of Item 1, wherein the system including a plurality of the image generating units;

wherein the switching operation unit is provided at least on one of the image generating units; and wherein the controller stores one or more photographed images generated serially by the plurality of image generating units between preceding switching information and subsequent switching information inputted via the switching operation unit, linking the one or more photographed images with examination subject information on an examination subject.

Item 4.

The diagnosis aiding system of any one of Items 1 to 3, further including a reception processing unit that receives input of examination subject information on an examination subject/subjects and produces an examination subject list containing the examination subject information, wherein the controller checks the produced examination subject list with a generation order of photographed images to be generated by the image generating unit so as to determine the examination subject, and obtains examination subject information on the examination subject.

Item 5.

The diagnosis system of Item 4, wherein the reception processing unit adds a new examination subject to the examination subject list, upon receipt of examination subject information on the new examination subject and updates the examination subject list, and wherein, after the examination subject list is updated by the reception processing unit, the controller uses the updated examination subject list to determine an examination subject.

Item. 6

The diagnosis system of any one of Items 1 to 3, further including an information operation unit to input examination subject information to the controller, wherein the controller links the examination subject information inputted via the information operation unit with a photographed image/images.

According to Item 1, when photographing is serially performed through switching of examination subjects, it is easy to identify groups of photographed images to be serially generated through switching information, by the unit of an examination subject. Thus, the photographed image group of a single examination subject can be linked with examination subject information thereon in a batch, which improves the processing efficiency.

According to Item 2, an operator can carry out switching operation of an examination subject via the switching operation unit provided on the image generation unit, when image generation of a single examination subject is completed. Thus, the work efficiency is improved.

According to Item 3, even when photographed images of a single examination subject are serially generated by a plurality of image generating units, an operator can perform switching operation of an examination subject via a switching operation unit provided on a nearest image generating unit. Thus, the operation load on the operator is relieved.

According to Item 4, the examination subject corresponding to a photographed image/images can be easily determined with the examination subject list, and examination subject information to be linked with the photographed image/images can be obtained, from the examination subject list.

According to Item 5, it is possible to use an examination subject list having been updated in order to determine an examination subject and obtain examination subject information. Accordingly, even when a new examination subject is added to an examination subject list, it is possible to link examination subject information with a photographed image/images.

According to Item 6, it is possible to link examination subject information inputted by an operator with a photographed image/images. Thus, it is possible to individually add more detailed examination subject information and link it with a photographed image/images.

First, a structure will be described below.

FIG. 1 shows the system configuration of a diagnosis aiding system 1 in the present embodiment. The diagnosis adding system 1 is applied to a smaller-scale medical institution, such as a clinic, and aids a series of tasks from the reception of patients, examination photographing, diagnosis by a doctor, to accounting.

The diagnosis aiding system 1 is, as shown in FIG. 1, constituted with an image generating unit 2 including an ultrasonic photographing device 2a, endoscopic photographing device 2b, CR (Computed Radiography) photographing device 2c, controller 3, server 4, reception device 11a, and terminal 24. The respective elements are connected to be able to communicate with each other via a network 6, such as a LAN. For communication, DICOM (Digital Imaging and Communication in Medicine) standard is employed. Herein, the portable terminal 24 is connected wirelessly.

Figure 2:
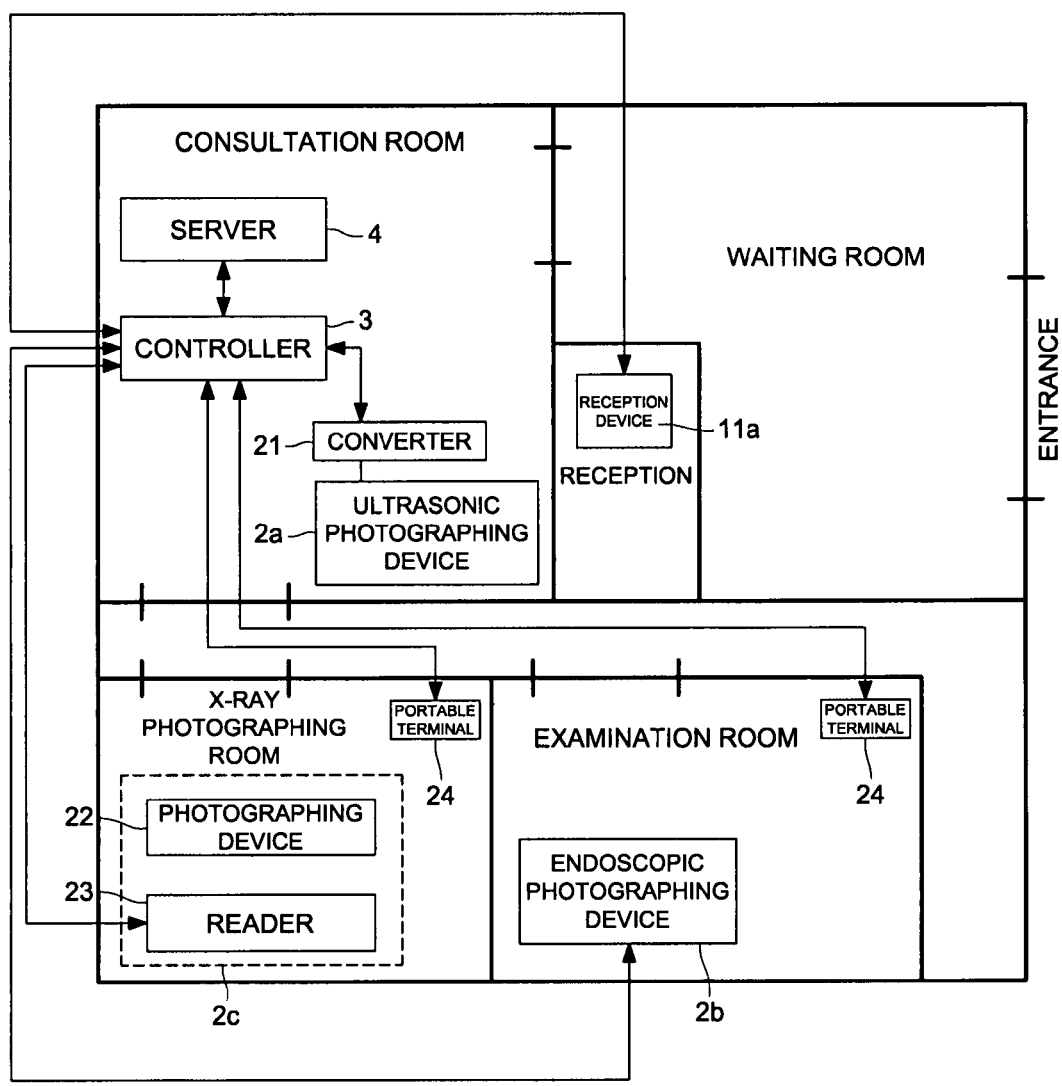
FIG. 2 is a diagram showing an example where the diagnosis aiding system, in FIG. 1, is applied to a small-scale medical institution.

FIG. 2 shows an example where the respective element devices of the diagnosis aiding system 1 are disposed in a medical institution.

The medical institution, shown in FIG. 2, is divided into plural areas of a waiting room, diagnosis room, X-ray photographing room, and examination room. The element devices are distributed across the respective areas. Concretely, disposed are the reception device 11a in the waiting room, the controller 3, server 4, and ultrasonic photographing device 2a in the diagnosis room, the endoscopic photographing device 2b in the examination room, and the CR photographing device 2c in the X-ray photographing room. Herein, the portable terminal 24 is carried by a doctor or assistant, and is not installed to a certain fixed position.

Following the reception procedure at the reception, a patient moves to the diagnosis room, and answers questions by the doctor. When it is determined that examination photographing is required, the patient moves to the photographing room and examination room, gets photographed and examined, and returns to the diagnosis room. Upon receipt of results of examination and photographing, the patient consults a doctor, and goes to the reception to pay a bill and receives a prescription. The diagnosis aiding system 1 is applied to a small-scaled medical institution where a series of these actions can be done with a relatively short movement, for example, on the same floor.

The respective element devices will be described below.

The reception device 11a is a reception computer that receives inputs of information on examination subjects, such as names and sexes of patients having been received, and processes the information. The reception device 11a assigns reception numbers to the received patients, on whom examination subject information has been input, as serial numbers in the order of reception, and lists up the examination subject information in the order of the reception number (The produced list is referred to as an examination subject list.). The data of the produced examination subject list is transmitted to the controller 3.

FIG. 3 shows an examination subject list (patient list).

The examination subject list shows a list of patients to be subjects of examination. As shown in FIG. 3, a simple list is formed where the examination subject information on the names of the patients, etc. are linked with the reception numbers. Herein, other items of examination subject information, such as sex and birth date, may be provided on the examination subject list.

Via the reception device 11a, a new patient is added to the examination information list upon each reception of a patient, and a patient is deleted from the examination subject list after each completion of accounting. Thus, the list is updated.

An updated list may be transmitted to the controller 3 upon each updating, or an updated list may be transmitted at a certain elapsed time as the list is then.

Further, when there are patients who are not subjects of examination, such as patients who visit the institution just to pick up drug and do not consult a doctor or patients for whom only observation is necessary, identification information is added for such patients on the examination subject list to show the situation. When transmitting an examination subject list to the controller 3, patients added with the identification information may be deleted from the list to be transmitted.

Further the reception device 11a also performs account processing. The reception device 11a is connected with a printer, and after completion of examination photographing and diagnosis, calculates diagnosis expenses for each patient, according to examination result information, diagnosis result information, prescription information, and the like inputted by an operator, and outputs a bill from the printer. The reception device 11a also prints out the prescription, according to the prescription information.

The controller 3 is a console for control operation by the doctor. Upon instruction operation by the doctor, the controller 3 performs image control, such as linking of reading processing conditions related to digitizing of photographed images by the image generating unit 2, image processing conditions of the photographed images, and the images (finished images) for diagnosis having been subjected to image processing, with the patient information of patients who are the subjects of the photographing. Further, the controller 3 functions as a viewer to display photographed images obtained by examination photographing.

Herein, an electric medical chart function enabling input of comments on diagnosis and schema, and report generation may also be implemented on the controller 3.

Figure 4:
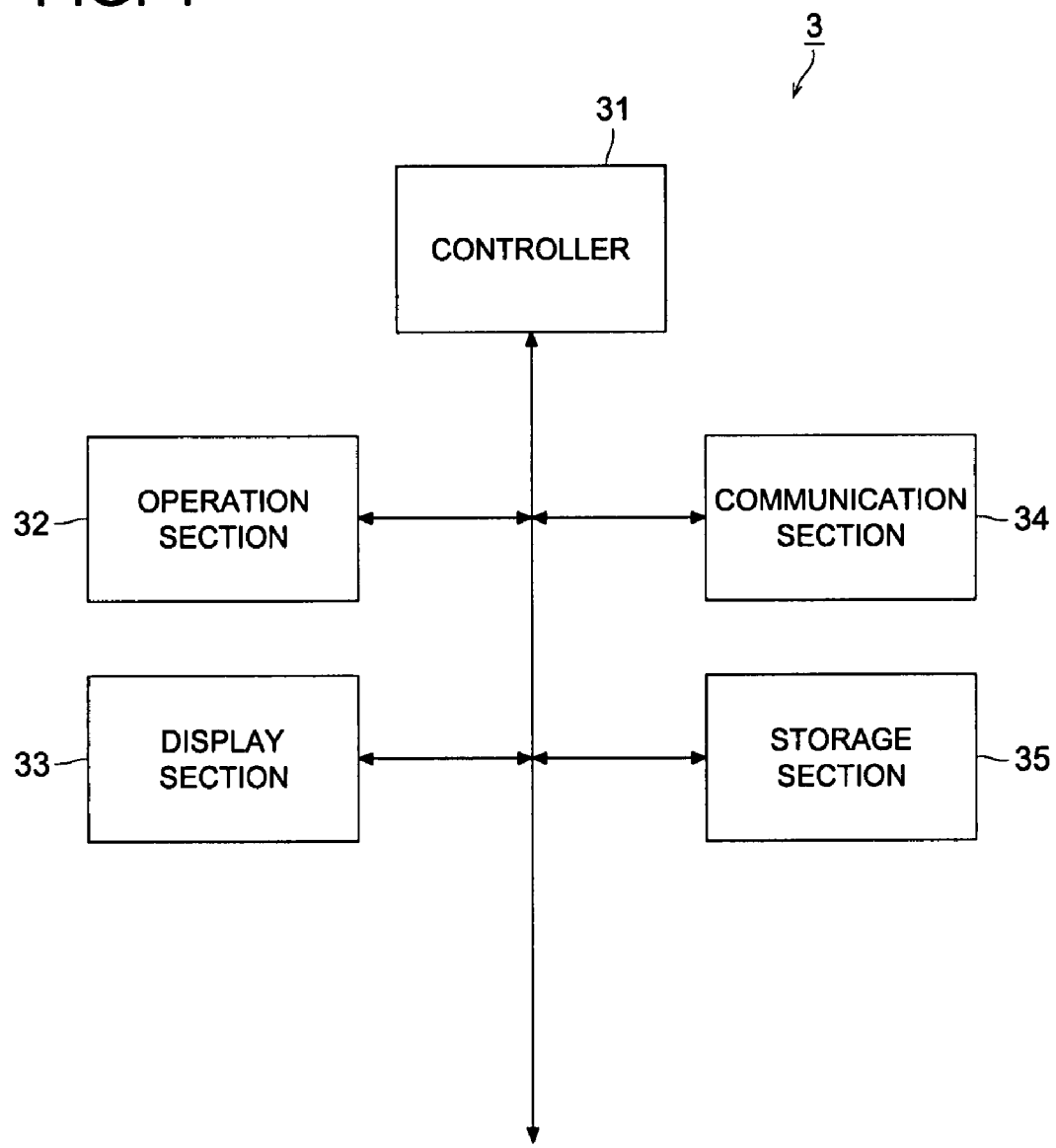
FIG. 4 is a diagram showing an inner structure of a controller, shown in FIG. 1.

FIG. 4 shows the inner structure of the controller 3.

As shown in FIG. 4, the controller 3 is configured with a control section 31, operation section 32, display section 33, communication section 34 and storage section 35.

The control section 31 is provided with a CPU (Central Processing Unit), RAM (Random Access Memory), etc., reads various control programs stored in the storage section 35, and executes various computation and central control of the respective sections 31 to 35 in collaboration with the control programs.

The operation section 32 has a keyboard and mouse, generates operational signals corresponding to operation of these, and outputs the signals to the control section 31.

The display section 33 is structured with a display, such as a LCD (Liquid Crystal Display), and performs various displays including an operation screen and photographed image, on the display, according to control by the control section 31.

The communication section 34 includes an interface for communication, such as a network interface card, and communicates with an external device on the network 6. For example, the communication section 34 receives data of photographed images from the image generating unit 2, and transmits processed images obtained by image processing of the photographed images, to the server 4.

The storage section 35 stores control programs and image processing programs executable by the control section 31, and parameters and data required by the respective programs.

Now, the image generating unit 2 will be described.

The image generating unit 2 generates data of photographed images of patients through photographing, and includes the ultrasonic photographing device 2a, endoscopic photographing device 2b, and CR (Computed Radiography) photographing device 2c. The data of photographed images generated by the image generating unit 2 is transmitted to the controller 3 upon each photographing.

The ultrasonic photographing device 2a is provided with an ultrasonic probe to output ultrasound. The ultrasonic photographing device 2a transmits ultrasound into a human body from the ultrasonic probe, receives an acoustic wave (echo signal) having reflected in the body organs by the ultrasonic probe again, and generates an image, according to the echo signal.

The ultrasonic photographing device 2a is connected with the network 6 via a converter 21 that performs conversion from analog signals to digital signals, and the like. The converter 21 performs conversion of a data format as well as the signal conversion, described above. For example, for data inputted from outside, a data format applied to the ultrasonic photographing device 2a and a data format applied externally are converted to each other.

The endoscopic photographing device 2b is provided with a photographing section having a small-sized camera at the tip end of a tube. The photographing section is constituted with optical devices, such as LED (Liquid Emitting Diode) for lighting, optical lens, and CCD (Charge Coupled Device), and photographs, with the CCD, an optical image formed by collection of light by the optical lens. The image signal obtained through the photographing is converted into a digital signal by a signal processing section and transmitted to the controller 3.

The CR photographing device 2c executes radiation photographing by the use of a cassette, and is constituted with the photographing device 22 and reader 23. The cassette houses a phosphor plate for detecting radiation, in a housing. Herein, a FPD (Flat Panel Detector) may be applied which directly generates image data corresponding to the X-ray amount. Photo-electro conversion devices are disposed in a matrix form in the housing of the FPD. In this case, the reader 23 is not provided, and data is extracted from the FPD in the photographing device 22 and transmitted to the controller 3.

The photographing device 22 is constituted with a radiation source, photographing table to mount a cassette, and the like. Radiation rays are projected to a patient from the radiation source, and radiation rays having transmitted through the patient are detected by the phosphor plate in the cassette.

Figure 5:
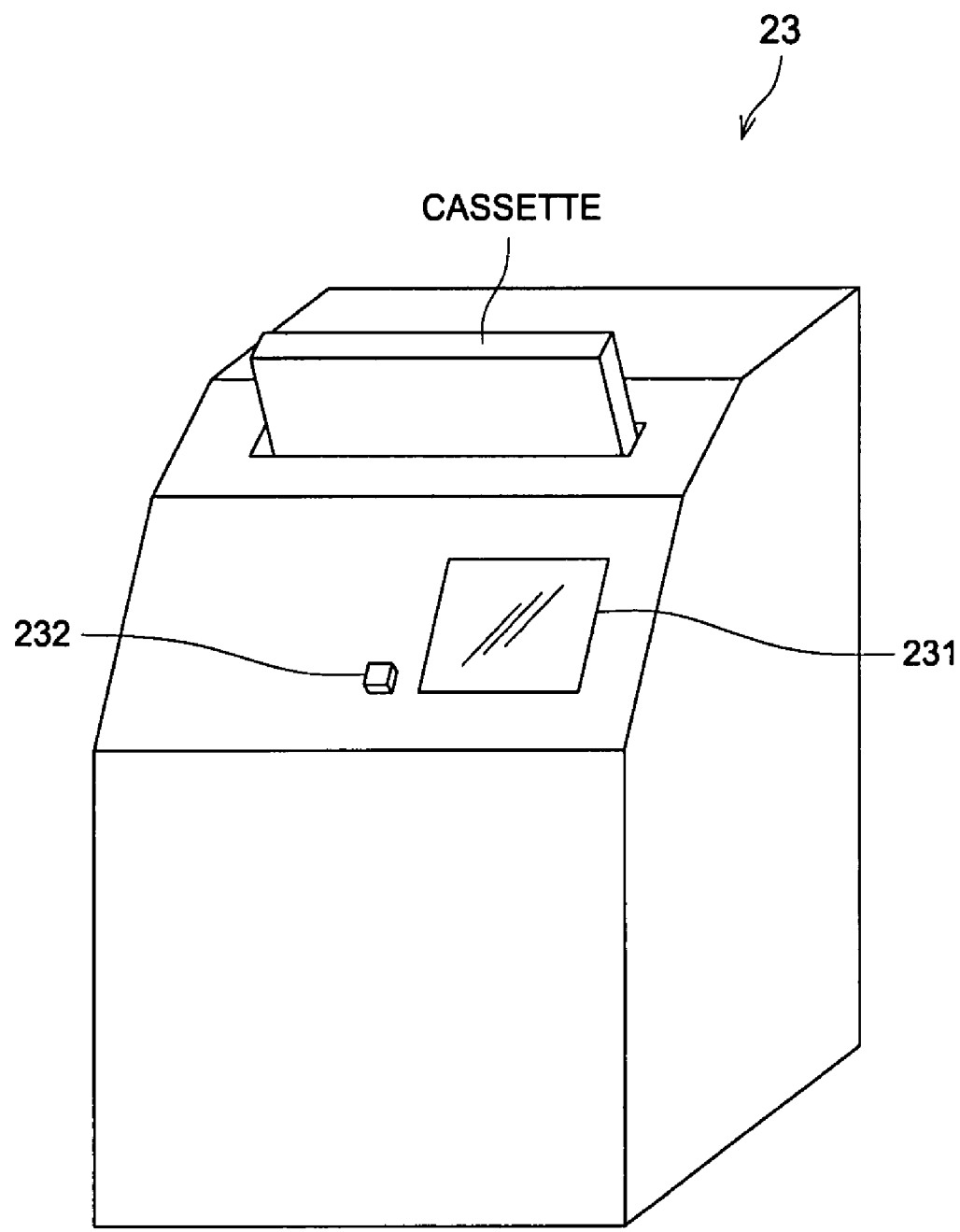
FIG. 5 is a diagram showing an example of a patient switching button provided on a reader, shown in FIG. 2.

The reader 23, as shown in FIG. 5, enables loading of a cassette thereon, and generates image data, corresponding to the amount of radiation detected by the phosphor plate. In the reader 23, there are arranged a control section for computation and control, a storage section, and also an image generating section that projects exciting light to the phosphor plate and photo-electrically converts the exciting light so as to generate an image signal (analog signal) corresponding to the amount of radiation, a signal processing section that performs signal processing on the analog signal and digitizes it.

Further, as shown in FIG. 5, a small display 231 and a patient switching button 232 are arranged on the upper portion. The display 231 displays a patient notification screen that notifies the patient who is the examination subject, as shown in FIG. 6, and other various screens, under control by the controller 3. The patient switching button is used to input switching information showing that the patient as the examination subject has been switched.

Each time the reader 23 reads a photographed image, the reader 23 transmits data of the photographed image to the controller 3. When the patient switching button 232 is operated, the reader 23 transmits, to the controller 3, switching information showing the timing at which the patient has been switched.

The server 4 includes a database 5 that stores photographed images, report information, electric medical chart, and the like, and integrally manages these data.

The portable terminal 24 is a portable type computer provided with a CPU, storage section, display section, communication section, and the like. For example, the portable terminal can be a PDA (Personal Digital Assistant), a note type PC (Personal Computer), or the like.

The portable terminal 24 receives an examination subject list or a patient notification screen, as shown in FIG. 6, and displays it.

Now, the operation of the above diagnosis aiding system 1 will be described, focusing on the operation of the controller 3, shown in FIG. 7.

First of all, when a patient has come for diagnosis, the reception device 11a performs reception processing on the patient. An operator (receptionist) asks the name of the patient and the like, and inputs it to the reception device 11a. Information input then is simple and enough to identify the patient, such as the name and sex.

The diagnosis aiding system 1 generates an examination subject list (refer to FIG. 3) showing a list of patients having been received, based on the examination subject information of the patients having been input via the reception device 11a. The generated examination subject list is transmitted to the controller 3 via the network 6.

Figure 7:
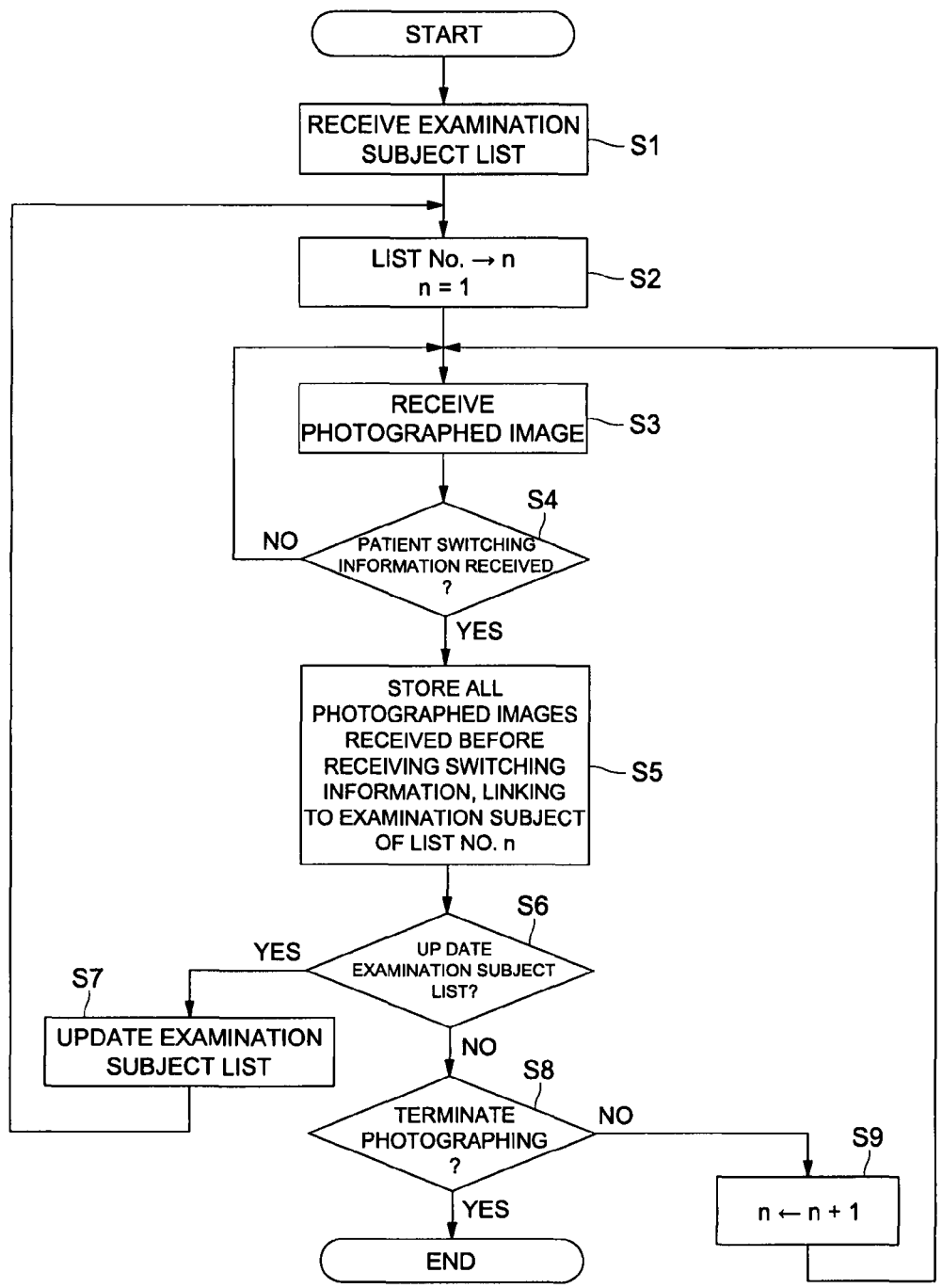
FIG. 7 is a flowchart illustrating the flow of processing by the controller.

When the examination subject list is received by the controller 3 (step S1), as shown in FIG. 7, the examination subject list is displayed on the display section 33 under control by the controller 3. On the examination subject list, the reception numbers and names of received patients who are waiting for diagnosis are displayed, as shown in FIG. 3, on a list. The reception numbers are those issued by the reception device 11a for temporary identification of the received patients, being serial numbers in the order of receiving the patients.

The doctor refers to the examination subject list displayed on the controller 3, confirms reception No. 1, which is the first one, namely the patient first received, directs the patient into the diagnosis room, and examines the patient. Then, if examination photographing is necessary, the flow proceeds to the photographing task to be executed by the image generating device 2. In the following, a case of performing radiation photographing with the CR photographing device 2c will be described. However, similar processing is executed also by another device, namely the ultrasonic photographing device 2a or endoscopic photographing device 2b. Herein, it is assumed that before photographing of a patient is completed, photographing of another patient is not executed.

On the other hand, upon receipt of the examination subject list by the controller 3, the control section 31 assigns list numbers 1 to m to the patients on the examination subject list in the order of the patients starting with the first patient. A list number n indicating the current examination subject (the patient who is in turn to have examination and diagnosis) is initially set to n=1 (step S2), and examination subject information (information of the patient's name and reception number) on the patient of list No. n is obtained from the examination subject list and transmitted to the CR photographing device 2c having a display 231.

On the CR photographing device 2c, a patient notification screen, as shown in FIG. 6, is displayed, according to examination subject information received from the controller 3, the patient notification screen indicating the name and reception number of the patient and thus indicating that the patient is the next examination subject. The doctor confirms the examination subject patient by this patient notification screen, and executes the photographing task.

The CR photographing device 2c carries out radiation irradiation, according to operation, and radiation photographing. In a case of performing photographing for plural times on a single patient, for example, changing the photographing direction, the cassette is replaced and thus serial photographing is performed. Thereafter, the plural cassettes used for photographing are sequentially loaded on the reader 23 of the CR photographing device 2c to be read. When all the cassettes have been read, the doctor operates the patient switching button 32.

On the reader 23, photographed images are read from the cassettes to generate data of them, which is transmitted to the controller 3. Then, when the patient switching button 23 is operated, switching information is generated and transmitted to the controller 3.

When the controller 3 sequentially receives the photographed images through the communication section 34 (step S3), and then, when the controller 3 has received switching information from the CR photographing device 2c (step S4; Y), the control section 31 determines that all the photographed images which had been received before the switching information has been received are for the patient of the list number n. Herein, all these photographed images are linked with the examination subject information (namely, the name and reception number of the patient in the present embodiment) of the list number n and then transmitted to the server 4 (step S5).

For example, the linkage is made by writing patient information to the header areas of the photographed images or by relating the file of the patient with the photographed images, and transmitting both the file and photographed images to the server 4.

On the server 4, the photographed images are stored in the database 5, based on the patient information linked with the photographed images having been transmitted.

Figure 8:
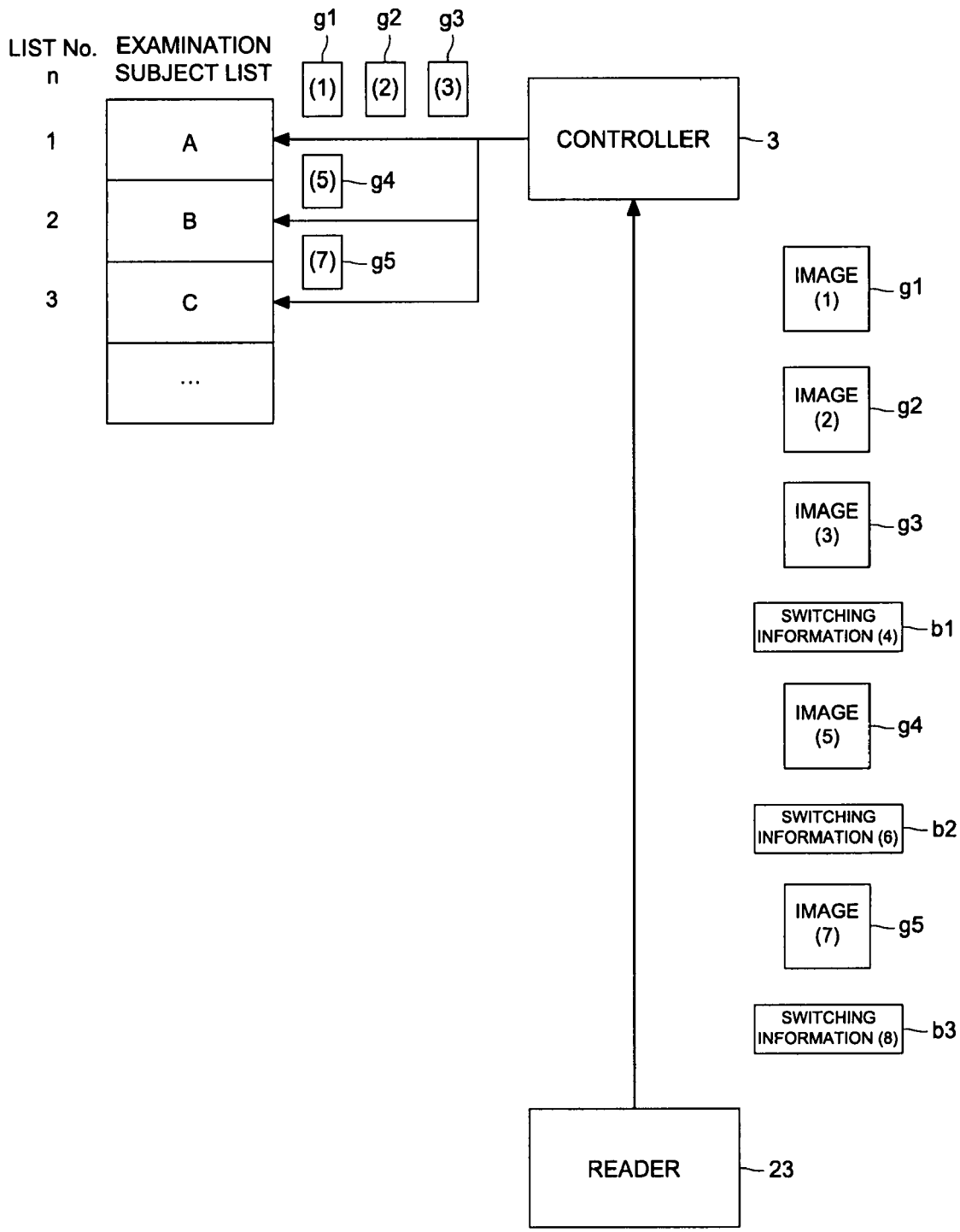
FIG. 8 is a diagram illustrating a method that links photographed images generated by a single image generating device and patients.

The above linkage will be described below in details, referring to FIG. 8.

When there are three cassettes for patient A of list No. 1, one cassette for patient B of list No, 2, and one cassette for patient C of list No. 3, the doctor presses the switching button 232 each time reading of the cassette/cassettes of one of the patients A to C is completed. Therefore, as shown in FIG. 8, data is input from the reader 23 to the controller 3 in the order of the three photographed images g1 to g3, switching information b1, one photographed image g4, switching information b2, one photographed image g5, and switching information b3. The numbers in the parentheses show the order of transmitting of the data.

The controller 3 links the photographed images with patient information in the order starting with patient A of list No. 1, and recognizes switching of the patient by switching information. Accordingly, the photographed images g1 inputted first, and g2 and g3 inputted prior to the input of swathing information b1, are recognized to be photographed images of the patient of list No. 1. Further, photographed image g4 inputted between the previous switching information b1 and the subsequent switching information b2 is recognized to be a photographed image of patient B of list No. 2. Likewise, photographed image g5 inputted between the previous switching information b2 and switching information b3 is recognized to be a photographed image of patient C of list No. 3.

In such a manner, during photographing of images g1 to g5 which are serially inputted, switching information b1 to b3 is inserted at a timing of switching patients, and thereby it is possible to easily identify photographed images corresponding to the respective patients by the controller 3. Further, for a patient with plural photographed images, it is possible to link the group of photographed images with the patient in a batch, which achieves a high processing efficiency.

Further, on the controller 3, the control section 31 determines whether to update the examination subject list (step S6). When an updated new examination subject list is input via the reception device 11a and accordingly the current examination subject list is to be updated (step S6; Y), the current examination subject list is overwritten with the new examination subject list so as to be updated (step S7), and then the flow proceeds to the processing in step S2. In other words, list No. n is initialized as n=1 on the updated examination subject list, and the processing in steps from S3 to S5 is repeated.

On the other hand, when the examination subject list is not updated (step S6; No), the control section 31 determines whether operation for instructing termination of photographing has been made (step S8). Herein, if such operation has not been made (step 8; N), then list No. n is incremented (step S9) by +1, and the flow proceeds to the processing in step S3 to repeat the processing in steps S3 to S6. With the increment of list No. n, it is determined in step S5 that photographed images generated from the next input are those for the next patient in step S5.

If operation for instructing termination of photographing has been made (step S8; Y), then the process is terminated.

As described above, in accordance with the present embodiment, by providing the patient switching button 232 on the reader 23 and operating it each time image generation is completed for a single patient, the controller 3 can recognize a group of photographed images, which are serially inputted, by the unit of a patient. Thus, a group of photographed images for a certain patient can be linked with patient information on the patient in a batch, improving the processing efficiency.

Further, since list numbers, which are not reception numbers, are assigned to examination subjects for linkage with photographed images, starting with the first examination subject, even when the reception list is updated, an examination subject can be identified by the use of the updated list.

In the present embodiment, there has been described a case where photographed images are serially inputted to the controller 3 only from the reader 23. However, the invention can be applied also to a case where photographed images are serially input from plural image generating devices, such as the ultrasonic photographing device 2a and endoscopic photographing device 2b. The numerals in the parentheses indicate the data input order to the controller 3. In this case, the patient switching button 232 may be arranged on any one of the plural image generating devices so as to operate the switching button 232 when photographing and image generation for one patient have been completed by the image generating devices.

Figure 9:
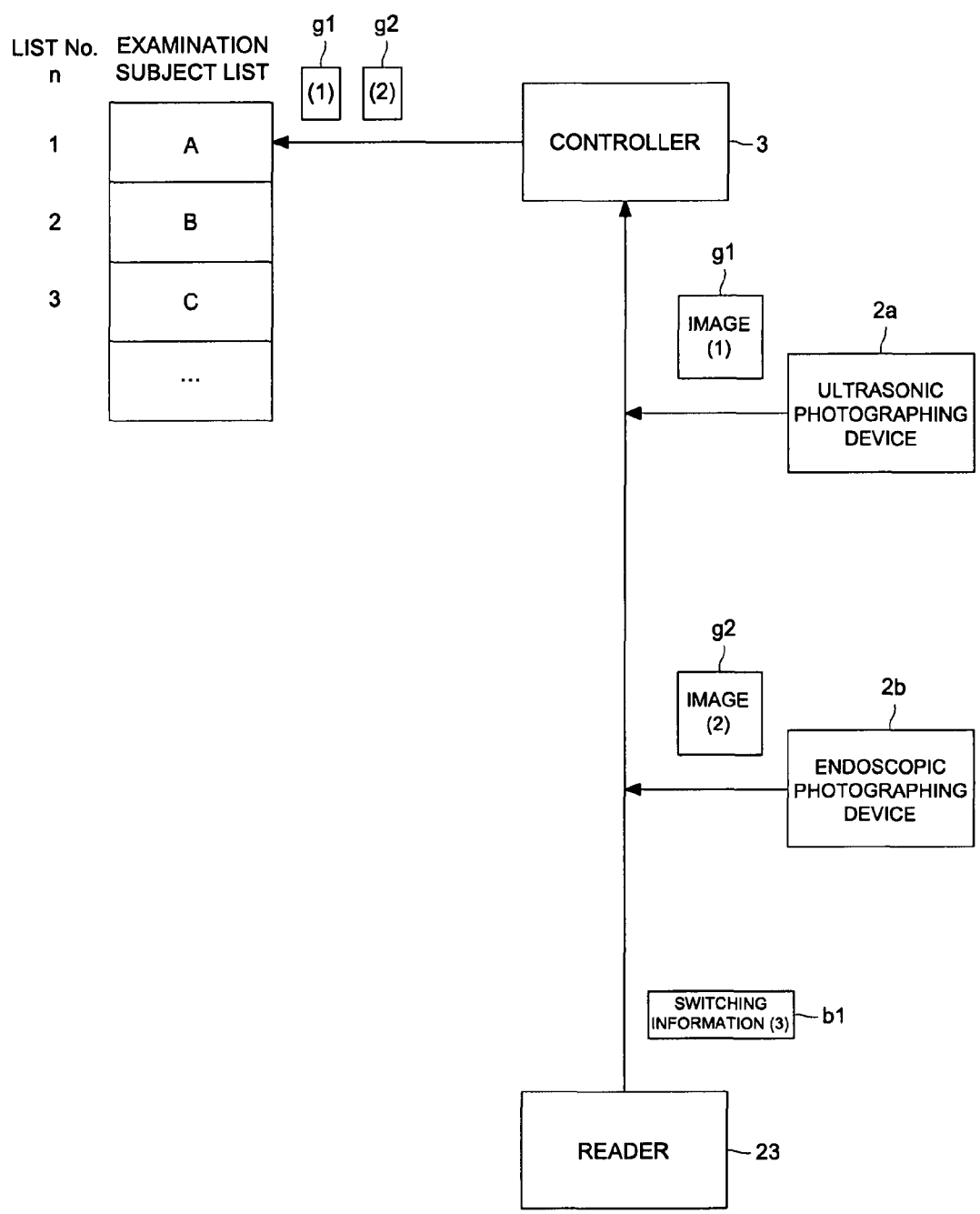
FIG. 9 is a diagram illustrating a method that links photographed images generated by plural image generating devices and patients.

As shown in FIG. 9, after photographed image g1 is input from the ultrasonic photographing device 2a and photographed image g2 is input from the endoscopic photographing device 2b, sequentially to the controller 3, switching information b1 is input from the reader 23 to the controller 3. Accordingly, the photographed images g1 and g2 which have been input before switching information is input are determined to be those of patient A of list number 1.

With such a constitution, even in a case where photographed images are input to the controller 3 from plural different image generating devices for a single patient, timing of switching the patient can be recognized. Consequently, even when photographed images in different sorts are obtained, groups of photographed images can be linked with examination subject information on corresponding examination subjects.

Figure 10:
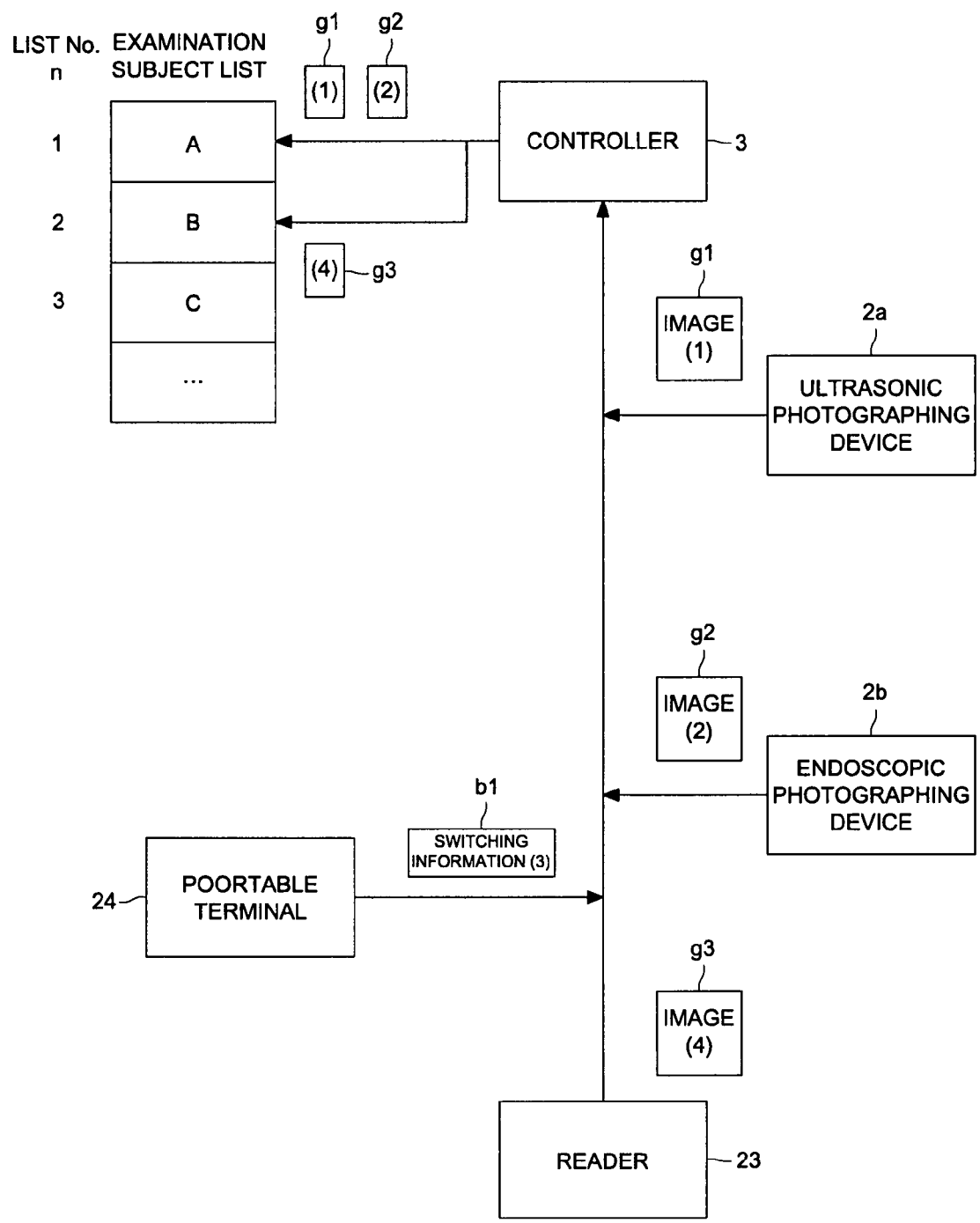
FIG. 10 is a diagram illustrating an example of practicing the method, shown in FIG. 9, where a patient switching button is provided on a portable terminal.

Further, as shown in FIG. 10, the patient switching button 232 may be arranged on the portable terminal 24 instead of an image generating device. In this case, the doctor does not need to move to the image generating device on which the switching button 232 is arranged each time photographing and image generation are completed for one patient, and the doctor can operate the patient switching button 232 at an arbitrary place, which improves the working efficiency of the doctor.

Still further, although examination subject information is obtained from an examination subject list and linked with photographed images, the invention is not limited thereto, and it is also allowed to form a structure which enables input of examination subject information via the operation section 32 of the controller 3 and linkage of such inputted examination subject information with photographed images. With such a structure, more detailed information on patients (for example, the birth dates, allergy types, etc. of patients) that the doctor obtains by diagnosis or the like can be linked with photographed images.

What is claimed is:

1. A diagnosis system for use with an examination subject, comprising:
    a plurality of image generating apparatuses structured to photograph the examination subject and to generate data of a photographed image of the examination subject;
    an input unit to input examination subject information;
    a switching operation unit to input switching information on the examination subject;
    a storage unit; and
    a controller, connecting to the plurality of the image generating apparatuses, the input unit, the switching operation unit, and the storage unit, the controller being structured to receive data of the photographed image of the examination subject transmitted from the plurality of image generating apparatuses, examination subject information inputted from the input unit, and the switching information transmitted from the switching operation unit, wherein the data of the photographed image of the examination subject is not linked with the examination subject information of the examination subject, wherein the controller is further structured to store data of photographed images received from the plurality of image generating apparatuses into the storage unit between receipt of preceding switching information and receipt of subsequent switching information from the switching operation unit, and link the data of photographed images with the examination subject information on the examination subject inputted from the input unit.

2. The diagnostic system of claim 1, further comprising a plurality of image generating apparatuses of plural kinds, wherein the controller is connected to the plurality of the image generating apparatuses of plural kinds and receives data of photographed images generated therefrom, and the controller stores data of photographed images received from the plurality of the image generating apparatuses of plural kinds between receipt of preceding switching information and receipt of subsequent switching information from the switching operation unit, into the storage unit, linking with the examination subject information of the examination subject inputted from the input unit.

3. The diagnostic system of claim 2, wherein the plurality of the image generating apparatuses of plural kinds comprises at least two of the following three apparatuses: a radiographic apparatus, an ultrasonic apparatus, and an endoscopic apparatus.

4. The diagnostic system of claim 1, wherein at least one of the plurality of the image generating apparatuses is equipped with the switching operation unit.

5. The diagnostic system of claim 1, wherein the switching operation unit is arranged on a portable terminal device.

6. A diagnosis system for use with an examination subject, comprising:

a plurality of image generating apparatuses structured to photograph the examination subject and to generate data of a photographed image of the examination subject;

an input unit to input examination subject information;

a switching operation unit to input switching information on an examination subject;

a storage unit; and a controller, connecting to the plurality of image generating apparatuses, the input unit, the switching operation unit, and the storage unit, and structured to receive data of the photographed image of an examination subject transmitted from the image generating apparatuses, examination subject information inputted from the input unit and switching information transmitted from the switching operation unit, wherein the data of the photographed image of the examination subject is not linked with the examination subject information of the examination subject;

wherein the controller is further structured to store data of photographed images received from the plurality of image generating apparatus into the storage unit, and link the data of photographed images with the examination subject information of the examination subject inputted from the input unit, and the controller is structured to change the examination subject information, which is linked to generated data of photographed image, each time when the controller receives switching information from the switching operation unit.

7. The diagnostic system of claim 6, further comprising a plurality of the image generating apparatuses of plural kinds, wherein the controller is connected to the plurality of the image generating apparatuses of plural kinds and receives data of photographed images generated therefrom, and the controller stores data of photographed images received from the image generating apparatuses into the storage unit, linking with the examination subject information of the examination subject inputted from the input unit, and the controller changes the examination subject information, which is linked to generated data of photographed images, each time when the controller receives switching information from the switching operation unit.

8. The diagnostic system of claim 7, wherein the plurality of the image generating apparatuses of plural kinds comprises at least two of the following three apparatuses: a radiographic apparatus, an ultrasonic apparatus, and an endoscopic apparatus.

9. The diagnostic system of claim 6, wherein at least one of the plurality of the image generating apparatuses is equipped with the switching operation unit.

10. The diagnostic system of claim 6, wherein the switching operation unit is arranged on a portable terminal device.

* * * * *